United States Patent [19]
Schafer

[11] 4,052,572
[45] Oct. 4, 1977

[54] HEARING AID

[75] Inventor: Curtiss R. Schafer, Newtown, Conn.

[73] Assignee: Electro-Physical Research, Inc.

[21] Appl. No.: 681,429

[22] Filed: Apr. 29, 1976

[51] Int. Cl.² .......................................... H04R 25/00
[52] U.S. Cl. ............................................. 179/107 R
[58] Field of Search ........................................ 179/107

[56] References Cited
U.S. PATENT DOCUMENTS 2,703,344  3/1955  Anderson .................. 179/107 BC

*Primary Examiner*—George G. Stellar

[57] ABSTRACT

"Hearing" without involving the ear is realized by electrical conduction of the sound-representing signals on a carrier optimally in the frequency range of 15–60 kHz, from an electrode held against a person's head to the auditory cortex and possibly to the auditory nerve. This is here called a "cortical hearing aid". The ability of the person to recognize sounds with a cortical hearing aid is notably enhanced by introduction of significant distortion of the audio signals, especially low-order harmonics of the audio frequencies. The distortion acts as a substitute for distortion ordinarily occurring in the ear but disregarded in the hearing process.

10 Claims, 1 Drawing Figure

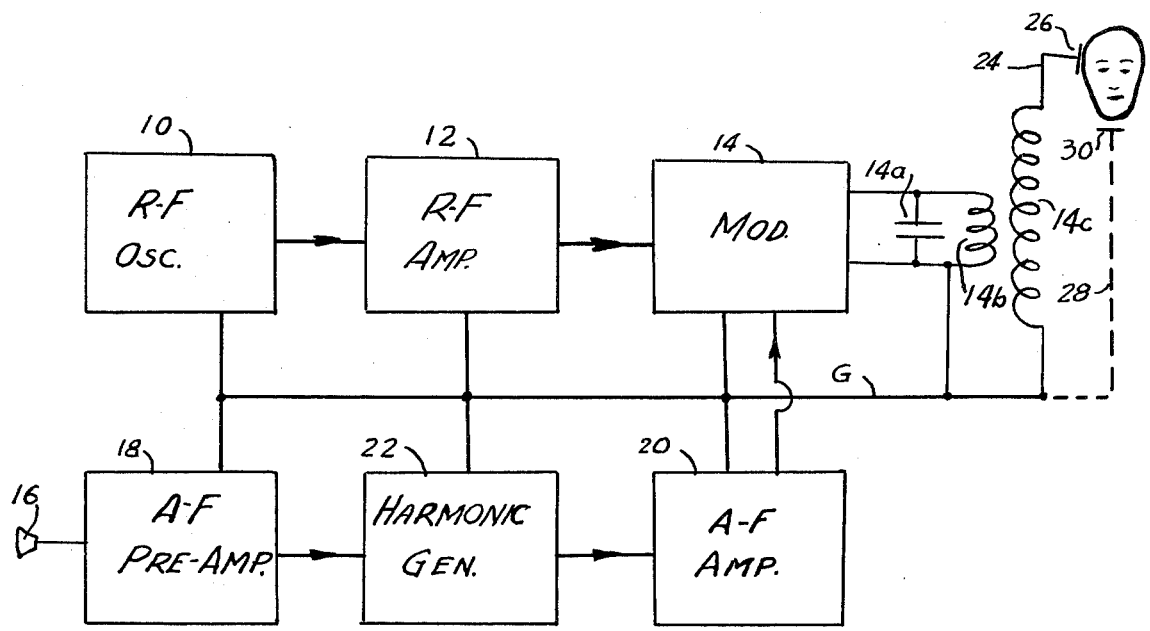

HEARING AID

FIELD OF THE INVENTION

This invention relates to hearing aids, and in particular to purely electrical hearing aids in contrast to electro-acoustical hearing aids.

BACKGROUND OF THE INVENTION

The form of hearing aid widely used currently by people with hearing defects depends on applying acoustic energy to the subject, commonly in the ear canal but in some cases in a manner that depends on bone conduction of sound waves. Various forms of hearing aids have also been proposed of the type wherein electrical or electro-magnetic energy (rather than acoustic energy) is applied to the subject. Such hearing aids are primarily intended for persons whose hearing impairment is such that acoustic hearing aids work poorly or not at all. Those proposed hearing aids purportedly transmit electro-magnetic energy to the facial nerves or the auditory cortex of the user. Efforts have been made to market a hearing aid of the type in U.S. Pat. No. 3,393,279 issued July 15, 1968, but I am informed that, after deliberate efforts, that device is no longer being sold. Recognizing the fact that some deaf people are unable to hear with electro-acoustic hearing aids and are thus wholly dependent on some other type of hearing aid, it is apparent that there is a pressing need for a non-acoustical hearing aid that is effective.

SUMMARY OF THE INVENTION

An object of the present invention resides in the provision of a novel and effective non-acoustic hearing aid. Such a hearing aid is useful to many people with hearing defects and it is indispensable to certain people whose hearing does not respond to acoustic hearing aids. Non-acoustic hearing aids are also useful to people having unimpaired hearing, for secret communication to them or to enable communication to persons with normal hearing while their hearing is securely baffled against high ambient noise.

The illustrative embodiment of the invention described below represents a novel effective cortical hearing aid. It includes means for providing a carrier frequency signal modulated by the audio signal to be "heard". The carrier frequency in the example below is 33 kHz, in an optimum range of 15–60 kHz. The audio signal is subjected to a substantial percentage of distortion, notably harmonic distortion.

The described device has high load-circuit impedance and relatively high output voltage, and it has a resonant output circuit having a high ratio of capacitance to inductance. These features render the flow of current in the subject largely independent of body impedance variations in any one person and among various individuals, enhancing the hearing aid.

Studies have shown that the normal hearing process involves notable nonlinearity in the cochlea. The distortion components of the sound developed in the ear tend to become masked or suppressed or disregarded, but they are inherently present. In a cortical hearing aid, the cochlea is bypassed, but the signal to the auditory cortex approximates the usual signal to the auditory nerve. A hearing aid made in accordance with the invention was subjected to test on many individuals. With few exceptions, the hearing aid used in the test improved the speech discrimination of the people in the test as compared with results when they used their usual acoustic hearing aids of various designs. Some of the subjects in the test were unable to hear, unaided, and obtained impressive scores in the tests. The success of the relatively unrefined cortical hearing aid in the test is particularly impressive since it is compared with results obtained from the same subjects using commercial hearing aids perfected over many years of production and widespread use. The devices constructed under the Flanagan patent, supra, contrasted with the test unit most notably in the prominent distortion present in the test unit of the present invention.

The nature of the invention and its various novel aspects and advantages will be better understood from the following detailed description of the illustrative embodiment shown in the accompanying drawing. In the drawing:

The single FIGURE is a block diagram of an illustrative embodiment of the invention.

THE ILLUSTRATIVE EMBODIMENT

In the drawing, an oscillator 10 operating at a frequency in the optimal range 15–60 kHz is coupled through an isolating amplifier 12 to a modulator 14. A microphone 16 and pre-amplifier 18 provide an audio signal that is to be "heard". This signal is supplied to audio amplifier 20 which is coupled to modulator 14 in a manner to yield a modulated carrier.

The modulator may assume various conventional forms.

A harmonic generator 22 is diagrammatically illustrated as interposed between pre-amplifier 18 and amplifier 20. The form and location of the harmonic-producing means are subject to a wide range of variation. Many transistors, as well as pentodes and beam power tubes, generate harmonics ranging up to the 14th. Where these devices are operated in push-pull circuitry, the even harmonics are cancelled out (or nearly so), leaving the odd harmonics. Controlled percentages of even harmonics can be developed by using an unbalanced push-pull stage. Amplifier 20 itself may be designed to provide such characteristics, thus incorporating the harmonic generator 22 that is diagrammatically illustrated as a separate component. In refining the performance of such a circuit for present purposes, inverse feedback loops may be included to discriminate in favor of or against low or high order harmonics. In an example, a triode on one side of a push-pull stage and a pentode or a beam power tube on the other side of the stage may be used in order to achieve a proper blend of even and odd harmonics.

A triode tube or a transistor as a single-ended stage operated class AB tends to generate an abundance of odd and even harmonics, predominantly the third and fifth. An amplifier operating at or near saturation can serve to develop odd and even low-order harmonics (e.g. 2 to 5) useful for present purposes. Saturated magnetic cores can also be used for this purpose.

A hearing aid in accordance with the invention involved a harmonic generator in the modulator itself. That modulator was of the Heising type, in which modulation takes place in the anode circuit of a modulator tube. It was operated class AB, producing 100% modulation.

In the drawing, the resonant "tank" circuit of the modulator includes a capacitor 14a in parallel with a coil 14b, having a high ratio of capacitance to inductance. Coil 14b is also the primary winding of a step-up transformer having a secondary winding 14c. One terminal of winding 14c is connected to the common system ground G, forming the common signal reference connection of all the other components 10, 12 ... 22. A wire 24 extends to a disc electrode 26. A further wire 28 (shown dotted, because it is optional) extends to another disc electrode 30.

In operation of this apparatus, the unmodulated carrier level at electrode 26 was 500 volts, yielding a 1000-volt signal when 100% modulated, as measured by a Ballantine AC meter. Disc electrode 26 was about one inch in diameter or a bit larger, and covered with several layers of adhesive cellophane tape. In a modification, a bare electrode was used, but a capacitor of 0.000035 mfd was interposed in wire 24 as a series impedance. The electrode surface should be chemically neutral on the skin of the wearer, so that if the electrode is not covered with insulation, it should be gold-plated or otherwise rendered inactive chemically.

Electrode 26 was placed against the head of each wearer in a test, in position for maximum response. This position in most instances was about one inch forward and above the ear canal, opposite the auditory cortex of the brain. With twenty-five subjects tested, the following table gives the results:

tion score for the 25 subjects unaided was 38.08%, it was 82.06% with conventional hearing aids; and it was 91.76% with the test cortical hearing aid. Twenty-two subjects (88%) attained the criterion of normal speech discrimination (90-100% correct responses) with the test cortical hearing aid; eleven subjects (44%) met this criterion using their conventional hearing aids; and one subject (4%) met the criterion without a hearing aid.

In the cortical hearing aid used in the test, harmonic distortion was approximately 20% for a single tone. Intermodulation of speech tones and of music tones was estimated at about 40%. These figures represent ample levels of distortion for present purposes. However, a greater amount of distortion than the 3% present in the electric circuit of ordinary sound reproducers is required, preferably greater than about 5% harmonic distortion.

In the tests, both electodes 26 and 30 were used. Electrode 30 without electrode 26, when placed against any area of the subject provides no response. The device using electrode 26 without electrode 30 performs well, nearly as well in many subjects as when both electrodes are used. This indicates that the return current path in space from the subject's whole body to the common ground of the system does not interpose a disabling

| | | | DEGREE OF LOSS | | TYPE | SPEECH DISCRIMINATION | | |
|---|---|---|---|---|---|---|---|---|
| SUBJECT | AGE | SEX | RIGHT | LEFT | OF LOSS | No Aid | Con H/A | Test CHA |
| | | | (db) | (db) | | (%) | (%) | (%) |
| 1 E.L. | 68 | F | 45 | 43 | SN | 62 | 98 | 100 |
| 2 M.E. | 58 | F | 51 | 46 | SN | 58 | 90 | 100 |
| 3 C.R. | 52 | F | 53 | 46 | SN | 76 | 84 | 100 |
| 4 A.C. | 49 | M | 67 | 70 | MIX | 0 | 98 | 100 |
| 5 M.B. | 70 | F | 76 | 18 | SN | 0 | 84 | 100 |
| 6 F.S. | 71 | M | 48 | 56 | SN | 52 | 84 | 92 |
| 7 P.R. | 58 | M | 52 | 66 | SN | 46 | 96 | 100 |
| 8 M.H. | 60 | F | 42 | 46 | C | 90 | 100 | 100 |
| 9 P.P. | 58 | M | 53 | 60 | SN | 42 | 80 | 100 |
| 10 O.M. | 70 | M | 56 | 56 | SN | 0 | 76 | 94 |
| 11 K.M. | 10 | F | 73 | 48 | MIX | 34 | 56 | 100 |
| 12 D.T. | 11 | M | 61 | 65 | SN | 0 | 100 | 100 |
| 13 N.T. | 9 | F | 101 | 93 | SN | 0 | 58 | 0 |
| 14 C.C. | 61 | M | 45 | 65 | SN | 64 | 88 | 96 |
| 15 M.H. | 14 | F | 40 | 48 | SN | 58 | 80 | 92 |
| 16 D.R. | 52 | F | 56 | 56 | SN | 60 | 82 | 90 |
| 17 A.R. | 17 | M | 110+ | 61 | SN | 0 | 72 | 94 |
| 18 M.W. | 14 | M | 44 | 48 | SN | 66 | 94 | 100 |
| 19 F.C. | 39 | M | 62 | 60 | SN | 0 | 90 | 98 |
| 20 J.B. | 58 | F | 53 | 45 | SN | 58 | 74 | 98 |
| 21 J.S. | 26 | M | 48 | 56 | SN | 56 | 92 | 100 |
| 22 C.M. | 70 | M | 56 | 56 | SN | 0 | 76 | 56 |
| 23 R.P. | 47 | F | 51 | 41 | SN | 70 | 96 | 100 |
| 24 A.C. | 66 | F | 43 | 47 | SN | 60 | 90 | 100 |
| 25 R.R. | 55 | M | 45 | 38 | MIX | 0 | 86 | 84 |

In the table, SN means sensorineural loss of hearing, and C means conductive hearing loss. The test was conducted at a rehabilitation center by its director, a certified audiologist. The last three columns indicate, respectively, test results with no hearing aid, with the conventional hearing aids of the subjects, and with the cortical hearing aid described above. Under controlled conditions, each subject was asked to repeat fifty phonetically balanced words. During the test, electrode 30 was placed against the subject's neck. Stimulus electrode 26 was excited by a 1000 Hz test signal and the location of the electrode was selected when the subject reported hearing the tone the loudest.

Twenty of the twenty-five subjects showed better speech discrimination with the above-described cortical hearing aid than with their conventional hearing aids. In two subjects, the results were unchanged. Only three subjects obtained better discrimination scores with their conventional hearing aids. The mean speech discriminaamount of impedance.

It has been noted above that the impedance of the output circuit is high. This results largely from the small capacitance of the insulation-covered stimulus electrode 26 to the subject and its correspondingly high impedance at the carrier frequency. High impedance can also be introduced otherwise, as by an interposed small capacitor mentioned above. Especially when the load-circuit impedance is high, it becomes unnecessary to have a resonant circuit close-coupled to the output circuit and in that case, there is no C/L ratio to be concerned about.

The foregoing embodiment of the invention is illustrative, and it is evidently subject to a latitude of rearrangement and modification by those skilled in the art. Consequently, the invention should be construed broadly in accordance with its full spirit and scope.

What is claimed is:

1. A cortical hearing aid comprising a source of audio frequency signals, means for providing a carrier-frequency signal, a modulator responsive to the audio frequency signal source and the carrier-frequency signal means to provide a modulated carrier-frequency signal, and means including an electrode coupled to the modulator and adapted to be placed against a subject's head to couple the modulated signal into the subject, said hearing aid including means for imposing harmonic distortion greater than 5% on the audio frequency signal.

2. A cortical hearing aid in accordance with claim 1, wherein the total distortion in the low-order harmonics of a single-frequency tone is in the range of about 5% to 20% of the audio-frequency signal strength.

3. A cortical hearing aid in accordance with claim 1, wherein the unmodulated carrier signal is about 500 volts at said electrode and the load circuit includes current-limiting impedance independent of the body impedance of the subject.

4. A cortical hearing aid in accordance with claim 1, wherein the carrier frequency is in the range of about 15-60 kHz.

5. A cortical hearing aid in accordance with claim 1 for enabling a person to sense with discrimination electrical signals representing the everyday spectrums of frequencies including speech and music, wherein said source of audio frequency signals includes a microphone and wherein said hormonic distortion is substantially greater than 5%.

6. A cortical hearing aid in accordance with claim 5, wherein the total distortion in the low-order harmonics of a single-frequency tone is in the range of 5% to about 20% of the audio-frequency signal strength, and wherein the carrier frequency is in the range of about 15-60 kHz.

7. The method of enabling a person to effect cortical sensing and recognition of a variety of sounds including speech and music, including the steps of providing an electrical signal having a spectrum of audio frequencies, providing a carrier-frequency signal, modulating the carrier-frequency signal with said electrical signal, impressing the output of the modulator on an electrode coupled to the person's head so as to effect cortical sensing of the spectrum of audio frequencies, said method including the step of imposing harmonic distortion of at least 5% on said electrical signal.

8. The method of claim 7 wherein the total distortion in the low-order harmonics of a single-frequency tone is in the range of 5% to about 20% of the audio-frequency signal strength.

9. The method of claim 7 wherein the carrier frequency is in the range of about 15-60 kHz.

10. The method of claim 7 wherein the total distortion in the low-order harmonics of a single-frequency tone is in the range of 5% to about 20% of the audio-frequency signal strength, and wherein the carrier frequency is in the range of about 15-60 kHz.

* * * * *